United States Patent
Sift Carter

(10) Patent No.: US 8,013,011 B2
(45) Date of Patent: Sep. 6, 2011

(54) TREATMENT AND PREVENTION OF BENIGN PIGMENTED MOLES (NAEVI) USING ARTEMISININE AND THE DERIVATIVES THEREOF

(75) Inventor: Rosemarie Sift Carter, Basel (CH)

(73) Assignee: EPIPHARM GmbH, Basel (CH)

(*) Notice: Subject to any disclaimer, the term of this patent is extended or adjusted under 35 U.S.C. 154(b) by 367 days.

(21) Appl. No.: 12/089,773

(22) PCT Filed: Oct. 19, 2006

(86) PCT No.: PCT/CH2006/000583
§ 371 (c)(1),
(2), (4) Date: Apr. 10, 2008

(87) PCT Pub. No.: WO2007/045116
PCT Pub. Date: Apr. 26, 2007

(65) Prior Publication Data
US 2008/0255223 A1   Oct. 16, 2008

(30) Foreign Application Priority Data

Oct. 20, 2005 (CH) .................................. 1686/05
Mar. 30, 2006 (CH) .................................. 0514/06

(51) Int. Cl.
*A61K 31/357* (2006.01)
*A61K 31/36* (2006.01)
*C07D 493/22* (2006.01)
*A61P 17/00* (2006.01)

(52) U.S. Cl. .................... 514/450; 549/348; 424/443

(58) Field of Classification Search .................... 424/443
See application file for complete search history.

(56) References Cited

U.S. PATENT DOCUMENTS

| | | | | |
|---|---|---|---|---|
| 4,191,767 A * | 3/1980 | Warner et al. | ................. | 514/250 |
| 4,978,676 A | 12/1990 | Thornfeldt | | |
| 5,905,089 A * | 5/1999 | Hwang et al. | ................. | 514/468 |
| 6,127,405 A * | 10/2000 | Kumar et al. | ................. | 514/450 |
| 6,130,254 A * | 10/2000 | Fisher et al. | ................. | 514/725 |
| 2002/0106384 A1* | 8/2002 | Zhang et al. | ................. | 424/401 |
| 2002/0182166 A1* | 12/2002 | Martin et al. | ................... | 424/74 |
| 2005/0119232 A1 | 6/2005 | Haynes | | |
| 2005/0187189 A1 | 8/2005 | Hartell et al. | | |

FOREIGN PATENT DOCUMENTS

| | | |
|---|---|---|
| EP | 0 428 773 | 5/1991 |
| WO | 95/15783 | 6/1995 |
| WO | 95/34262 | 12/1995 |

OTHER PUBLICATIONS

Galal A.M. et al., "Antifungal Activity of Artemisinin Derivatives," Journal Natural Products, vol. 68, No. 8, pp. 1274-1276 (2005).
Tromberg J. et al., "Congenital melanocytic nevi needing treatment," Dermatologic Therapy, vol. 18, No. 2, pp. 136-150 (2005).

* cited by examiner

*Primary Examiner* — Richard Schnizer
*Assistant Examiner* — Audrea Buckley
(74) *Attorney, Agent, or Firm* — Greenblum & Bernstein, P.L.C.

(57) ABSTRACT

A method of treating a benign pigmented mole or a dermatomycosis. The method comprises locally applying to a subject in need thereof artemisinine and/or one or more structurally related compounds. Also disclosed is a plaster which comprises a topical formulation comprising artemisinine and/or one or more structurally related compounds.

13 Claims, No Drawings

TREATMENT AND PREVENTION OF BENIGN PIGMENTED MOLES (NAEVI) USING ARTEMISININE AND THE DERIVATIVES THEREOF

BACKGROUND OF THE INVENTION

1. Field of the Invention

The present invention relates to the treatment of benign pigmented moles (naevi) of the skin and mucous membranes; in particular nevus cell nevi, of lentigos and pigmented nevi of the mucous membranes with locally applied, but in particular with topical formulations. Furthermore, it relates to topical formulations which are suitable for this purpose.

2. Discussion of Background Information

The term nevus cell nevi means different benign skin changes, pigmented moles (birthmark, liver spot) that are composed in cellular terms of so-called nevus cells. Nevus cells are a defective development of the normal pigment-forming cells, the melanocytes. Melanocytic nevi occur in different number, size and color intensity in virtually all human beings. The outward appearance of nevi can be very different. They can be pigmented moles lying at the skin level or raised above the skin level (rounded, pediculate or flat) punctiform but also large-scale, wart-like, uneven or smooth, and the color ranges from skin-colored to brown to black. The number of melanocytic nevi acquired increases over the course of life. Nevus cell nevi with conspicuous structure have an increased risk of degeneration and are called dysplastic or atypical nevus cell nevi.

A malignant melanoma, that is black skin cancer, may possibly develop from a nevus cell nevus. In over 60 percent of all cases it develops from a nevus cell nevus. In recent decades a clear increase in the incidence of melanoma has been registered. While in the U.S. in 1960 a lifetime risk of approx. 1:600 was assumed, today one of 1:100 is observed. Thus, according to Dr. Matthias Volkenandt (Clinic for Dermatology and Allergiology of Ludwig-Maximilian University, Munich, Frauenlobstrasse 9, 80337 Munich), for example, melanoma has an incidence in the region of Bavaria of approx. 14 (i.e., 14 new cases) per 100,000 inhabitants a year. This corresponds to a lifetime risk of approx. 1% (every $100^{th}$ person will be diagnosed with a melanoma in the course of his/her life). Given this figure, melanoma is not the most frequent tumor in humans, but the rise in the incidence according to Volkenandt is greater than with any other tumor.

According to the current level of knowledge, there is no preventative treatment or therapy that combats the degeneration of nevus cell nevi. Nevi with an increased risk of degeneration are chiefly surgically removed. Laser treatment plays more of a role in cosmetic aspects. Both methods are invasive, associated with certain risks (scarring, skin discoloration, etc.) and high costs.

The development of an acquired nevus is always preceded by a small, sometimes microscopically small, red spot (a bleeding or hemangioma). From this nevus precursor a larger red, somewhat raised mole frequently develops. From the nevus precursors then the brown nevus cell nevi develop, of different size, brown color and structure.

Artemisinine (also called qinghaosu) is a sesquiterpene lactone with a peroxide group, which has hitherto been examined and used mainly as a systematically active antimalarial drug. Artemisinine is very hard to dissolve in water; however, water-soluble derivatives of artemisinine have been developed. The systemic or topical use of artemisinine and derivatives thereof for the treatment of psoriasis, diseases of viral origin (warts, molluscum contagiosum and ovinia), ultraviolet radiation-induced diseases (polymorphous light dermatosis, "collagen vascular disease", premalignant keratosis, Bowen syndrome, lentigo maligna, basal-cell carcinoma, squamous cell carcinoma and malignant melanoma), vesicular skin diseases and hemorrhoids is described in EP-A-O 428 773.

SUMMARY OF THE INVENTION

The object of the present invention is to provide locally acting, but preferably topical formulations that are effective against benign pigmented moles, in particular against melanocytic nevi and thus can also be used in the prevention of skin cancer.

The object is attained according to the invention in that active ingredients from a class of compounds with the formula (I):

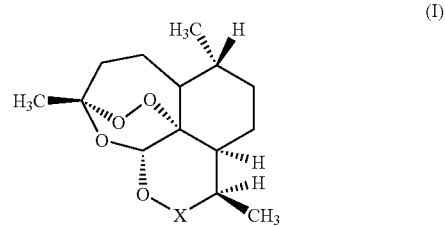

in which formula (I) X represents CO, CHOZ or CHNRZ, where Z is chosen from:

hydrogen; straight-chain and branched ($C_1$-$C_6$) alkyl; straight-chain or branched ($C_2$-$C_6$) alkenyl; straight-chain or branched ($C_2$-$C_6$) alkynyl; ($C_3$-$C_8$) cycloalkyl; ($C_6$-$C_{24}$) aryl; ($C_7$-$C_{24}$) aralkyl; m- and p-$CH_2(C_6H_4)$COOM; $COR^3$; $CSR^3$; $C(NR^6)R^3$; $SOR^4$; $SO_2OM$; $SO_2NR^7R^8$; $SO_2$O-artemisinyl; $SO_2$NH-artemisinyl; $POR^4R^5$ and $PSR^4R^5$; wherein $R^3$ is straight-chain or branched ($C_1$-$C_6$) alkyl; straight-chain or branched ($C_1$-$C_6$) alkoxy; straight-chain or branched ($C_2$-$C_6$) alkenyl; straight-chain or branched ($C_2$-$C_6$) alkynyl; ($C_3$-$C_8$) cycloalkyl; ($C_6$-$C_{24}$) aryl; ($C_6$-$C_{10}$) aryloxy; ($C_7$-$C_{24}$) aralkyl; —$(CH_2)_n$—COOM, with n as an integer from 1 through 6; or 10α-di-hydroartemisinyl;

$R^4$ and $R^5$ are selected independently of one another from straight-chain or branched ($C_1$-$C_6$) alkyl; straight-chain or branched ($C_2$-$C_6$) alkenyl; straight-chain or branched ($C_2$-$C_6$) alkynyl; ($C_3$-$C_8$) cycloalkyl; ($C_6$-$C_{24}$) aryl; ($C_7$-$C_{24}$) aralkyl; OM; straight-chain or branched ($C_1$-$C_6$) alkoxy; ($C_6$-$C_{10}$) aryloxy and $NR^7R^8$;

$R^6$ is selected from straight-chain or branched ($C_1$-$C_6$) alkyl; straight-chain or branched ($C_2$-$C_6$) alkenyl; straight-chain or branched ($C_2$-$C_6$) alkynyl; ($C_3$-$C_8$) cycloalkyl; ($C_6$-$C_{24}$) aryl and ($C_7$-$C_{24}$) aralkyl;

M is hydrogen or a pharmaceutically acceptable cation; and $R^7$ and $R^8$ independently of one another are hydrogen or straight-chain or branched ($C_1$-$C_6$) alkyl, or $R^7$ and $R^8$ together form a ($C_4$-$C_6$) alkylene bridge; and R is selected from hydrogen and the groups listed for $R^6$;

are used to produce the locally applied, in particular topical formulation against benign pigmented moles.

DETAILED DESCRIPTION OF THE INVENTION

Surprisingly, it was found that pigmented moles of the skin, in particular those of melanocytic origin, can be successfully treated locally very early with the above-referenced active agents, in particular with topical (e.g., cutaneous) preparations. It was also found that the prevention of skin cancer (in particular basal cell carcinoma or melanoma) is possible through the treatment of nevus cell nevi with compounds of formula (I). Furthermore, it was found that these active agents are also effective with local application in the prevention of benign pigmented moles, in particular of acquired nevus cell nevi.

Within the scope of the present application, "benign pigmented moles" are understood to be in particular:

nevi, in particular nevus cell nevus (banal or dysplastic; the nevus cell nevus is also often called melanocytic nevus); including its three subtypes that can be differentiated by place of origin, junction nevus cell nevus (boundary zone epidermis/dermis), compound nevus cell nevus (connective tissue of the dermis) and dermal nevus cell nevus (deep layers of the dermis), and its subtypes that can be differentiated according to time of occurrence, congenital nevus cell nevus (=birthmark) and acquired nevus cell nevus. A subgroup of acquired nevus cell nevi are recurrent nevi, which develop after the surgical removal of another benign birthmark. One example of a congenital junction nevus cell nevus is the Naevus Spilus, an example of an acquired junction nevus cell nevus or compound nevus cell nevus is the halo nevus (Naevus Sutton); and examples of acquired melanocytic junction nevus cell nevi, compound nevus cell nevi or dermal nevus cell nevi are the Naevus Spitz and the Naevus Reed. An example of a congenital dermal nevus cell nevus is the Mongolian spot (=Naevus Bleu) and an example of a congenital compound nevus cell nevus or dermal nevus cell nevus is the congenital giant pigment nevus (Naevus gigantus);

lentigos (such as liver spots—lentigo simplex, freckles=lentigo solaris, age spots —lentigo senilis, PUVA lentigos);

disorders of the melanin pigmentations (such as freckles=ephelides); and pigmented moles of the mucous membranes (such as connective tissue nevus in the eye, nevus on the lips and oral mucosa and on reproductive organs).

The compounds of formula (I) are effective in the treatment of all above-mentioned benign pigmented moles, in particular the acquired or congenital nevus cell nevi. Among the above-mentioned nevi, the dysplastic (atypical) nevus cell nevi have a higher probability of degenerating to skin cancer and are therefore nevi that are preferably treated with compounds of formula (I) to prevent skin cancer.

For the ($C_1$-$C_6$) alkyl, methyl, ethyl, n-propyl, i-propyl, n-butyl, sec-butyl, t-butyl, n-pentyl, sec-pentyl, neo-pentyl, n-hexyl, sec-hexyl and neo-hexyl are preferred. More preferably is a straight-chain ($C_1$-$C_3$) alkyl, and particularly preferred is methyl or ethyl. For the straight-chain or branched ($C_2$-$C_6$) alkenyl, ($C_2$-$C_4$) alkenyls, such as vinyl, allyl, 1-methylvinyl, 2-methylvinyl, but-1-en-1-yl, but-2-en-1-yl, but-3-en-1-yl, but-1-en-2-yl, but-2-en-2-yl, but-3-en-2-yl, 2,2-dimethylvinyl and 1,2-dimethylvinyl are preferred. For the straight-chain or branched ($C_2$-$C_6$) alkynyl, e.g., ethynyl, propargyl, prop-1-yn-1-yl, but-1-yn-1-yl, but-2-yn-1-yl, but-3-yn-1-yl, but-3-yn-2-yl, 3-methylbut-1-yn-1-yl, 3,3-dimethylbut-1-yn-1-yl, 1,1-dimethylbut-2-yn-1-yl and 1,1-dimethylprop-2-yn-1-yl are preferred. For the ($C_3$-$C_8$) cycloalkyl, cyclopropyl, cyclobutyl, cyclopentyl and cyclohexyl are preferred. For the ($C_6$-$C_{24}$) aryl, ($C_6$-$C_{10}$) aryls, such as phenyl, naphth-1-yl and naphth-2-yl, are preferred. For the ($C_7$-$C_{24}$) aralkyl, ($C_7$-$C_{12}$) aralkyls, such as benzyl, phenethyl, (naphth-1-yl)methyl and (naphth-2-yl)methyl, are preferred. For the alkyl in ($C_1$-$C_6$) alkoxy, the same radicals are preferred as exemplified above for ($C_1$-$C_6$) alkyl. Preferably it is a ($C_1$-$C_3$) alkoxy, and more preferably it is methoxy, ethoxy or n-propoxy. For the aryl in ($C_6$-$C_{10}$) aryloxy the same radicals are preferred as exemplified above for the ($C_6$-$C_{24}$) aryl. More preferably it is phenoxy or α- or β-naphthoxy.

Within the scope of the present application, the term "artemisinyl" denotes a group of formula (I) where X=CH—, so that this group can be bound to the oxygen or the nitrogen via the free valence of the carbon. Within the scope of the present application, the term "10-α-dihydroartemisinyl" denotes —O-artemisinyl, where artemisinyl has the above meaning.

In formula (I), for Z hydrogen; straight-chain or branched ($C_1$-$C_6$) alkyl, m- and p-$CH_2(C_6H_4)$COOM; $COR^3$; $SOR^4$; $SO_2OM$; $SO_2NR^7R^8$; $SO_2NH$-artemisinyl and $POR^4R^5$ are preferred.

For the pharmaceutically acceptable cation as M, for example, cations of alkali metals, e.g., of lithium, sodium or potassium, or alkaline earth metals, e.g., of magnesium and calcium, ammonium, and $H^+N(R^XR^YR^Z)$ can be mentioned by way of example, wherein $R^X$, $R^Y$, $R^Z$ independently of one another can be methyl or ethyl.

For Z as $COR^3$ it is preferred if $R^3$ is a straight-chain or branched ($C_1$-$C_6$) alkyl; straight-chain or branched ($C_1$-$C_6$) alkoxy; —$(CH_2)_n$—COOM or artemisinyl. In particular, for M here hydrogen, sodium, potassium or ammonium is preferred.

For Z as $SO_2OM$ it is preferred if M is an alkali metal, an alkaline earth metal or ammonium.

For Z as $POR^4R^5$ it is preferred if $R^4$ and $R^5$ are selected from OM and straight-chain or branched ($C_1$-$C_6$) alkoxy. More preferably one of $R^4$ and $R^5$ is OM, wherein the M is in particular sodium, potassium or ammonium, and the other one straight-chain or branched ($C_1$-$C_6$) alkoxy or OH.

The compounds of formula (I) are known or can be produced analogously to known compounds of formula (I). The compound where X=CO is the artemisinine, and the compound in which X=CHOH is the dihydroartemisinine. The compounds in which X=CHOZ, with Z different from hydrogen, or wherein X=CHNRZ, are referred to below as "derivatives of dihydroartemisinine."

The compounds of formula (I) can be obtained as follows:

Artemisinine (X=CO) can, as is known, be isolated from the plant *Artemisia Annua*.

Dihydroartemisinine (X=CHOH) is known and can be produced, for example, through the reduction of artemisinine with sodium borohydride in methanol at approx. 0° C.

The derivatives of dihydroartemisinine, where X=CHOZ, wherein Z is a straight-chain or branched ($C_1$-$C_6$) alkyl, straight-chain or branched ($C_2$-$C_6$) alkenyl, straight-chain or branched ($C_2$-$C_6$) alkynyl, ($C_3$-$C_8$) cycloalkyl, ($C_6$-$C_{24}$) aryl or ($C_7$-$C_{24}$) aralkyl; can be produced from dihydroartemisinine, in that it is first converted with trimethylsilyl chloride into its trimethylsilyl ether, the trimethylsilyloxy group is exchanged with trimethylsilyl bromide for bromine (according to Example 1 of US-A-2005/0119232), and then the bromine atom is in turn substituted in the presence of a base with an HOZ which if desired is used in an excess, wherein Z has the indicated meaning. Among these derivatives artemether (Z=Me) and arteether (Z=Et) are known compounds.

The derivatives of dihydroartemisinine, where X=CHNRZ, wherein R has the meaning indicated for formula (I) and Z=hydrogen, straight-chain or branched ($C_1$-$C_6$) alkyl, straight-chain or branched ($C_2$-$C_6$) alkenyl, straight-chain or branched ($C_2$-$C_6$) alkynyl, ($C_3$-$C_8$) cycloalkyl, ($C_6$-$C_{24}$) aryl or ($C_7$-$C_{24}$) aralkyl; can be produced from dihydroartemisinine, in that this is first converted with trimethylsilyl chloride into its trimethylsilyl ether, the trimethylsilyloxy group is exchanged for bromine with trimethylsilyl bromide (according to Example 1 of US-A-2005/0119232) and then the bromine atom, in turn, is substituted in the presence of a base with an amine HNRZ which if desired is employed in an excess, wherein R and Z have the indicated meaning.

The derivatives of dihydroartemisinine, where X=CHOZ or CHNRZ, wherein R has the meaning indicated with formula (I) and Z=m- or p-$CH_2(C_6H_4)$COOM (definition of M as given for formula (I)), are available from dihydroartemisinine or the derivative of dihydroartemisine where X=CHNRH, in that they are alkylated with m- or p-bromomethyl benzoic acid methyl ester in the presence of a base, followed by hydrolysis of the methyl ester and suitable salt formation, if M is not to be hydrogen. Among these derivatives, the derivative where X=CHOZ and Z=p-$CH_2(C_6H_4)$COOH is known as "artelinic acid".

The derivatives of dihydroartemisinine, where X=CHOZ or is CHNRZ, R having the meaning indicated with formula (I), Z=$COR^3$ or means $CSR^3$ and $R^3$ is straight-chain or branched ($C_2$-$C_6$) alkoxy or ($C_6$-$C_{10}$) aryloxy, can be produced by reacting dihydroartemisinine or the derivative of dihydroartemisinine where X=CHNRH with the suitable chlorocarbonic acid-($C_1$-$C_6$) alkyl ester or chorocarbonic acid-($C_6$-$C_{10}$) aryl ester or chlorthiocarbonic acid-($C_1$-$C_6$) alkyl ester or chlorthiocarbonic acid-($C_6$-$C_{10}$) aryl ester and a base.

The derivatives of dihydroartemisinine, where X=CHOZ or is CHNRZ, wherein R has the meaning indicated with formula (I), Z=$COR^3$ and $R^3$ is a straight-chain or branched ($C_1$-$C_6$) alkyl, straight-chain or branched ($C_2$-$C_6$) alkenyl, straight-chain or branched ($C_2$-$C_6$) alkynyl; ($C_3$-$C_8$) cycloalkyl, ($C_6$-$C_{24}$) aryl or ($C_7$-$C_{24}$) aralkyl; can be produced by reacting dihydroartemisinine or the derivative of dihydroartemisinine where X=CHNRH with an acyl chloride and a base, wherein the acyl chloride is substituted with the suitable $R^3$.

The derivatives of dihydroartemisinine, where X=CHOZ or is CHNRZ, R having the meaning indicated with formula (I), Z=$CSR^3$ and $R^3$ is a straight-chain or branched ($C_1$-$C_6$) alkyl, straight-chain or branched ($C_2$-$C_6$) alkenyl, straight-chain or branched ($C_2$-$C_6$) alkynyl; ($C_3$-$C_8$) cycloalkyl, ($C_6$-$C_{24}$) aryl or ($C_7$-$C_{24}$) aralkyl; can be obtained by reacting the corresponding derivative described above where Z=$COR^3$ with Lawesson's reagent.

The derivatives of dihydroartemisinine, where X=CHOZ or is CHNRZ, R having the meaning indicated with formula (I), Z=$COR^3$ and $R^3$ is —$(CH_2)_n$—COOM (M having the meaning indicated with formula (I)), can be prepared by reacting dihydroartemisinine or the derivative of dihydroartemisinine where X=CHNRH with a cyclic acid anhydride (if n=2 or is 3) or with MeOOC—$(CH_2)_n$—COOMe. In the latter case in the case where X=CHOZ a basic catalyst such as $NEt_3$ can also be used, and the methyl alcohol released during the transesterification can be withdrawn from the equilibrium, such as by evaporation under reduced pressure. If M is not hydrogen, a corresponding salt formation can follow, in that the remaining methyl ester group is split, e.g., with M-cyanide. Among these derivatives, the one where X=CHOZ, n=2 and M=hydrogen is known as "artesunate".

The derivatives of dihydroartemisinine, where X=CHOZ or is CHNRZ, R having the meaning indicated with formula (I), Z=$CSR^3$ and $R^3$ is —$(CH_2)_n$—COOM (M having the meaning indicated with formula (I)), can be produced in that in MeOOC—$(CH_2)_n$—COOMe one of the two carbonyl oxygens is replaced by sulfur with Lawesson's reagent and this hemithio-diester is reacted with dihydroartemisinine or the derivative of dihydroartemisinine where X=CHNRH, followed by hydrolysis of the still free —COOMe group to COOH and corresponding salt formation, if M is not hydrogen.

The derivatives of dihydroartemisinine, where X=CHOZ or is CHNRZ, R having the meaning indicated with formula (I), Z=$C(NR^6)R^3$ ($R^6$ having the meaning indicated with formula (I)) and $R^3$ is a straight-chain or branched ($C_1$-$C_6$) alkoxy or ($C_6$-$C_{10}$) aryloxy, can be obtained, in that an isocyanate $R^6$—NCO, in which $R^6$ has the indicated meaning, is reacted with a corresponding ($C_1$-$C_6$) alcohol or ($C_6$-$C_{10}$) aryl alcohol, and the urethane thus obtained is reacted with $POCl_3$ and then with dihydroartemisinine or the derivative of dihydroartemisinine where X=CHNRH in the presence of a base.

The derivatives of dihydroartemisinine, where X=CHOZ or is CHNRZ, R having the meaning indicated in formula (I), Z=$C(NR^6)R^3$ ($R^6$ having the meaning indicated with formula (I)) and $R^3$ is straight-chain or branched ($C_1$-$C_6$) alkyl, straight-chain or branched ($C_2$-$C_6$) alkenyl, straight-chain or branched ($C_2$-$C_6$) alkynyl; ($C_3$-$C_8$) cycloalkyl, ($C_6$-$C_{24}$) aryl or ($C_7$-$C_{24}$) aralkyl, can be obtained in that an isocyanate $R^6$—NCO, where $R^6$ has the indicated meaning, is reacted with a corresponding Grignard reagent $R^3$MgBr, where $R^3$ has the indicated meaning, and the amide thus obtained is reacted with $POCl_3$ and then with dihydroartemisinine or the derivative of dihydroartemisinine where X=CHNRH in the presence of a base.

The derivatives of dihydroartemisinine, where X=CHOZ or is CHNRZ, R having the meaning indicated with formula (I), Z=$C(NR^6)$ and $R^3$ is —$(CH_2)_n$—COOM (M and $R^6$ having the meaning indicated with formula (I)) can be obtained in that a compound MeOOC—$(CH_2)_n$—$CONHR^6$, wherein n and $R^6$ have the indicated meaning, are reacted with $POCl_3$ and then with dihydroartemisinine or the derivative of dihydroartemisinine where X=CHNRH in the presence of a base, and the methyl ester is hydrolyzed, and, if M is not hydrogen, a suitable salt formation is carried out.

The derivatives of dihydroartemisinine, where X=CHOZ or is CHNRZ R having the meaning indicated with formula (I)), where Z=$SOR^4$ and $R^4$=OMe, can be obtained by reacting dihydroaratemisinine with excess dimethyl sulfite (DRP 487253), optionally in the presence of a basic catalyst, and distillation of the released methanol and finally the excess dimethyl sulfite under reduced pressure.

The derivatives of dihydroartemisinine, where X=CHOZ or is CHNRZ, R having the meaning indicated with formula (I), and Z=$SOR^4$ ($R^4$ being a straight-chain or branched ($C_1$-$C_6$) alkoxy or ($C_6$-$C_{10}$) aryloxy), can be obtained through reaction of the corresponding derivative where X=CHOH or CHNRH with excess thionyl chloride and a suitable base, such as pyridine, removal of the excess thionyl chloride and subsequent reaction of the obtained sulfurous acid derivative with the corresponding straight-chain or branched ($C_1$-$C_6$) alcohol or ($C_6$-$C_{10}$) aryl alcohol in the presence of a suitable base, such as pyridine.

The derivatives of dihydroartemisinine, where X=CHOZ or is CHNRZ, R having the meaning indicated with formula (I) and Z=$SOR^4$ ($R^4$ being ($C_1$-$C_6$) alkyl, straight-chain or branched ($C_2$-$C_6$) alkenyl, straight-chain or branched ($C_2$-$C_6$) alkynyl, ($C_3$-$C_8$) cycloalkyl, ($C_6$-$C_{24}$) aryl or ($C_7$-$C_{24}$) aralkyl), can be obtained by reacting a Grignard reagent $R^4$MgBr, wherein $R^4$ has the indicated meaning, with excess thionyl chloride, removal of the excess thionyl chloride and subsequent reaction of the $R^4$—SOCl obtained with the corresponding dihydroartemisinine derivative where X=CHOH or CHNRH in the presence of a suitable base, such as pyridine.

The derivatives of dihydroartemisinine, where X=CHOZ or is CHNRZ, R having the meaning indicated with formula (I) and Z=$SOR^4$ ($R^4$ being $NR^7R^8$, and $R^7$ and $R^8$ having the meaning indicated with formula (I)) can be obtained by reacting an amine $HNR^7R^8$ with excess thionyl chloride, removal of the excess thionyl chloride, and subsequent reaction of the $RR^7R^8$NSOCl obtained with the corresponding dihydroartemisinine derivative where X=CHOH or CHNRH in the presence of a suitable base, such as pyridine.

The derivatives of dihydroartemisinine, where X=CHOZ or is CHNRZ, with Z=$SO_2$OM (M having the meaning indicated with formula (I)) can be obtained by reacting the corresponding derivative where X=CHOH or CHNRH with pyridine-sulfur trioxide complex and exchange of the pyridinium counterion of the sulfonate obtained for M.

The derivatives of dihydroartemisinine, where X=CHOZ or is CHNRZ, where Z=$SO_2NR^7R^8$ and R, $R^7$ and $R^8$ have the meaning indicated with formula (I), can be obtained by reacting the dihydroartemisinine derivative where X=CHOZ or CHNRH with 1 eq. of sulfuryl chloride in the presence of a base, such as, e.g., pyridine and subsequent reaction with 1 eq. of an amine $HNR^7R^8$, where $R^7$ and $R^8$ have the indicated meaning, in the presence of base such as pyridine.

The derivative of dihydroartemisinine, where X=CHOZ, where Z=$SO_2$O-artemisinyl, can be obtained by reaction of 2 eq. of dihydroartemisinine with 1 eq. of sulfuryl chloride in the presence of base such as pyridine.

The derivative of dihydroartemisinine, where X=CHOZ, where Z=$SO_2$NH-artemisinyl, can be obtained by reacting dihydroartemisinine with 1 eq. of sulfuryl chloride in the presence of base such as pyridine and subsequent reaction with 1 eq. of the artemisinine derivative where X=$CHNH_2$ in the presence of base such as pyridine. The derivative thus obtained is identical to the derivative where X=CHNHZ and Z=$SO_2$O-artemisinyl. From the derivative thus obtained, subsequently the derivatives of dihydroartemisinine where X=CHNRZ, R having the meaning indicated with formula (I) except for hydrogen, can be obtained by deprotonation on the sulfamido nitrogen and alkylation with an alkylbromide RBr, where R has the indicated meaning.

The derivative of dihydroartemisinine, where X=CHNHZ, where Z=$SO_2$NH-artemisinyl, can be produced according to Example 2 of US-A-2005/0119232. From this in turn the derivatives of dihydroartemisinine can be produced, where X=CHNRZ, R having the meaning indicated with formula (I) except for hydrogen, by deprotonation on one of the two sulfamido nitrogens and alkylation with an alkylbromide RBr, where R has the given meaning.

The derivatives of dihydroartemisinine, where X=CHOZ or CHNHZ, where Z=$POR^4R^5$ or $PSR^4R^5$, and R, $R^4$ and $R^5$ have the meaning indicated with formula (I), can be obtained in that first dihydroartemisinine or the dihydroartemisinine derivative where X=CHNRH is reacted with excess $POCl_3$ (or $PSCl_3$) and the excess $POCl_3$ (or $PSCl_3$) is removed by distillation. To the raw product obtained, where X=$CHOPOCl_2$ (or $CHOPSCl_2$) or $CHNRPOCl_2$ (or $CHNRPSCl_2$), depending on the type of radicals $R^4$ and $R^5$ to be introduced, these are introduced as Grignard reagent $R^4$MgBr/$R^5$MgBr (if $R^4$ and/or $R^5$ are to be ($C_1$-$C_6$) alkyl, straight-chain or branched ($C_2$-$C_6$) alkenyl, straight-chain or branched ($C_2$-$C_6$) alkynyl, ($C_3$-$C_8$) cycloalkyl, ($C_6$-$C_{24}$) aryl or ($C_7$-$C_{24}$) aralkyl)) in the form of an alcoholate $R^4O^-$/$R^5O^-$ (if $R^4$ and/or $R^5$ are to be straight-chain or branched ($C_2$-$C_6$) alkoxy or ($C_6$-$C_{10}$) aryloxy)) or in the form of amines $HNR^7R^8$ or in the form of water or hydroxide; with the provisos that these reagents are preferably added in the order of their increasing nucleophilicity and, if at least one is to be $R^4$ and/or $R^5$OM, the MOH necessary for this purpose is added as the last reagent.

With the compounds where X=CHOZ or CHNRZ, the configuration on this C atom (i.e., the $C_{10}$ atom of the sesquiterpene backbone) can be (R) or (S). The compound of formula (I) can also be used in the form of a $C_{10}$-epimer mixture, wherein the ratio of the two epimers can be caused by the preceding reduction of artemisinine and/or by the exchange of the $C_{10}$-hydroxyl group for a different hydroxyl derived from water or for one of the nucleophiles used in the syntheses.

Those active agents of the above formula (I) which are selected from artemisinine, dihydroartemisinine, the derivatives containing carboxyl groups (in particular artesunate), arthemeter, arteether, propylcarbonate of dihydroartemisinine and artelinic acid are preferred. Artemisinine, dihydroartemisinine and artesunate are particularly preferred.

The compounds of formula (I) can be used individually or as a combination of two or more of these compounds.

The compounds of formula (I), in particular artesunate, are also effective in the prevention of acquired nevus cell nevi. For the prevention of nevus cell nevi, the compounds of formula (I), in particular artesunate, are applied extensively over the entire skin, to skin zones with increased probability of the formation of nevi, or to already visible nevus precursors. Skin zones with increased probability of the formation of nevi are on the one hand skin areas that are more frequently exposed to UV radiation. On the other hand, such skin zones are often present in the vicinity of a nevus cell nevus already formed (e.g., in a radius of typically up to 5 cm around the nevus already present). The compounds of formula (I), in particular artesunate, thereby have the further advantageous property that they render visible already existing nevus precursors that are so weak that they are hardly visible to the naked eye. Under the action of the compounds of formula (I), the still invisible nevus precursors first form small red dots, which become dark to black after a few days and in part look like dark crystals sitting in pores. In favorable cases, a reflected light microscope examination of the skin regions at issue is therefore no longer necessary.

For application, the active agents of formula (I) can be formulated in a suitable formulation for local application, in particular for topical (cutaneous) application. The concentration of the active agents in the formulations (preparations)

produced is not particularly critical. Formulations with a concentration of approx. 0.1 to approx. 40% by weight, based on the formulation, can be produced. For the treatment of nevus cell nevi (congenital=birthmarks or acquired) the formulations preferably contain approx. 5 to approx. 20% by weight of the active agent, and particularly preferably they contain approx. 10% by weight, based on the formulation. For the prevention of the acquired nevus cell nevi, the formulations preferably contain up to approx. 5% by weight of the compound of formula (I), based on the formulation; more preferably they contain approx. 1 to approx. 5% by weight. The precise therapeutically required quantity of active agent depends on the active agent itself, the base used, the prepared galenic form (such as ointment, suspension, pastes, plaster, cream, gel, solution) and on the additives used and can be determined by one skilled in the art by simple effectiveness tests.

The duration of treatment of existing nevus cell nevi (congenital=birthmarks or acquired) depends on the type, size, structure, pigmentation and the age of the nevus. Preferably the treatments are carried out cyclically with high concentrations of the compound of formula (I). Initial reactions are often visible after the first few days of treatment. It can take up to several months before there is a clear improvement or change, which is shown by a fading or a disappearance of the nevus cell nevus. This period can be longer in the case of older patients, since the renewal of the epidermis takes much longer with increasing age.

For the prevention of acquired nevus cell nevi an application twice or three times is sufficient. Larger nevus precursors are preferably treated longer until the fading or disappearance of the nevus precursors.

The active agent of formula (I) should penetrate into the skin to different depths depending on the therapeutic approach:
  For the treatment of nevus cell nevi (congenital=birthmarks or acquired), the active agent preferably penetrates up to the upper dermis, depending on the type and age of the nevus.
  For the prevention of acquired nevus cell nevi, the active agent preferably penetrates through the epidermis up to the junction zone, the border between epidermis and dermis.

As formulation base for the active agents of formula (I) all bases which are usual for local formulations and are inert toward these agents are suitable. In particular such bases for topical formulations can be petrolatum, fats, waxes, fatty acid esters paraffins, oils, silicones and polymers thereof. Preferably the active agents are formulated with approx. 60 to approx. 99.9% by weight, more preferably with approx. 80 to approx. 95% by weight of formulation base, based on the finished formulation. If hydrophilic/aqueous topical formulation bases are used, such as, e.g., hydrogels, creams, the active ingredients can be protected from degradation by nano-encapsulation, enclosure in liposomes or complexing with, e.g., cyclodextrins. Regarding the complexing of artemisinine and derivatives thereof with cyclodextrins, reference is made by way of example to US-A-2005/187189.

Topical formulations with an anhydrous, single-phase base, e.g., a pure fat phase that is anhydrous, are referred to as ointments according to the German Pharmacopeia. Ointments in which the active agents of formula (I) are used according to the invention, thus consist of an ointment base of this type, which can contain the finely distributed active agent(s) for application to the skin.

If the topical formulation is to be an ointment, the formulation base can preferably consist of lipophilic constituents with an N-octanol/water partition coefficient at room temperature of approx. 1 to approx. $10^5$, more preferably approx. 10 to approx. $10^5$ and particularly preferably approx. 50 to approx. $10^4$. Examples of the formulation base are here, for instance, petrolatum, fats, waxes, fatty acid esters, paraffins, oils, silicones and polymers thereof (e.g., polydialkylsiloxanes, silicone elastomers, silicone waxes, silicone emulsifiers).

In the application of an ointment the active agent of formula (I) leaves the topical base surrounding it and penetrates into the skin. The lipophilic base adheres very well to the skin and forms a water-repellent layer to the outside. This layer likewise prevents water leaving the skin to the outside (occlusion effect). Through this effect the skin is kept moist and it heats up because less water can evaporate. Through the increased moisture, the skin also becomes more elastic, which promotes the absorption of active agent.

In contrast to the ointment, two-phase systems (aqueous and fat phase) are called creams. The compounds of formula (I) can also be formulated as a cream. The same substances are possible for the fat phase as are exemplified above for the ointment base. In addition to water, the aqueous phase can also optionally contain buffering agents that cause a pH of the aqueous phase well tolerated by the skin, or it can also contain known gel forming polymers, such as, e.g., hydroxypropylmethylcellulose, carboxymethylcellulose, polyvinyl alcohol with crosslinkers (such as borax or multivalent metal cations such as $Mg^{2+}$ or $Ca^{2+}$) and the like. For emulsification, conventional surface-active substances well tolerated by the skin such as, e.g., fatty acid mono and diglycerides, PEG-40 hydrogenated castor oil (Cremophor®) or lecithin can be used.

As auxiliary agents for topical formulations, conventional penetration accelerators (such as dimethylacetamide, dimethylformamide, propylene glycol, fatty alcohols, triethanolamine, dimethylsulfoxide, azones and the like) keratolytics to improve effectiveness (such as salicylic acid, urea, retinoids) and preservatives are possible. Additives generally serve to improve the effectiveness, stability, durability and consistency of a galenic form of administration.

The compounds of formula (I) are preferably formulated in topical formulations essentially free of penetration-enhancing substances. The compounds of formula (I) are also preferably formulated essentially free of ($C_5$-$C_{19}$) moncarboxylic acids, esters thereof and amides thereof. Within the scope of the present application, "essentially free" means that the topical formulation has less than 1% by weight, preferably less than 0.1% by weight of penetration-enhancing substances, based on the formulation.

All the derivatives with a carboxyl group, in particular artesunate, are preferred as compounds of formula (I) for pastes, ointments, creams, solutions, gels, spray or suspensions. The carboxyl group can thereby optionally be present in the form of the alkali metal, alkaline earth metal or ammonium salt.

The active agents of formula (I) for application onto or into the skin are preferably applied to a plaster in the form of a topical formulation, in particular in the form of a paste, ointment, suspension, solution, gel, spray or cream, particularly preferably in the form of an ointment. This plaster can optionally have a material which takes up or absorbs the topical formulation. However, the active agent can also be directly suspended or dissolved in an inert adhesive of the plaster; analogous to known plasters, such as for scopolamine (e.g., "Scopoderm TTS") or for estradiol (e.g., "Estraderm TTS"). In this manner active agents can be in contact with the location to be treated directly and over a longer period. In addition, an occlusion effect occurs, which improves the active agent penetration.

Further forms of application of the active agents of formula (I) would be pastes, solutions, suspensions, gels and creams and sprays. The semisolid or liquid formulations of the cited active agents can also be present in the form of a stick (e.g., like a felt tip for precise dosage) or a roller (with active agent in suitable base, solution, suspension, ointment, cream).

Further examples of local application forms that can be used according to the invention for the compounds of formula (I) are applicators that effect the penetration of the compounds of formula (I) into the skin or mucous membrane by means of ultrasound, by means of electric fields or by means of microneedles. Known applicators that use ultrasound and can be used according to the invention are disclosed, e.g., in U.S. Pat. No. 6,908,448, which is hereby incorporated by reference. Applicators that use electric fields for the application of the active agents (which therefore use the principle of iontophoresis) have been known for a long time. They are suitable according to the invention for those active agents of formula (I) that are saline, i.e., those where X is CHOZ or CHNRZ, Z being selected from m- and p-$CH_2(C_6H_4)COOM$, $SO_2OM$ and $POR^4R^5$, where one of $R^4$ and $R^5$ is OM and the other one is a straight-chain or branched ($C_1$-$C_6$) alkoxy or OH, and M represents a pharmaceutically acceptable cation. For known applicators with microneedles for the local application according to the invention of active agents to the skin, reference can be made by way of example to US-A-2005/065463, which is likewise incorporated by reference herein.

Another example of a local form of application that can be used according to the invention is a technique in which the skin is lifted by means of a suction cup at the location to be treated and on the raised portion of the skin a part of the layer thickness of the dermis is removed mechanically, such as with a blade. This portion of the skin with partially removed dermis is more permeable for compounds of formula (I) and permits the local treatment of deeper layers of the dermis at this location. The equipment necessary for this is described in WO-A-95/15783, incorporated by reference herein.

A low-risk, non-invasive preventative or therapeutic treatment of acquired nevus cell nevi or of acquired or congenital nevus cell nevi (=birthmarks) with artemisinine and derivatives thereof (dihydroartemisinine, arteether, arthemeter, artesunate semisynthetic derivatives thereof and synthetically analogous compounds) represents enormous progress in the treatment of nevus cell nevi and could drastically reduce the risk of skin cancer. The invention is thus of great significance not only medically but also socioeconomically. No allergic skin reactions to the compounds were observed with the described topical treatments with the compounds of formula (I), in particular artesunate. It is also remarkable that healthy tissue is not damaged and the treatment is painless and simple.

In view of the results obtained so far, it can be assumed that the local, in particular topical therapy with artemisinine and derivatives thereof is very effective and, considered in the long term, as prevention and treatment of nevi is more cost-effective and low-risk than traditional and invasive treatment methods.

The invention is now further illustrated by the following examples.

EXAMPLE 1

Topical Formulation 3 g of artesunate were stirred homogenously with 27 g of Exipial® fat ointment.

EXAMPLES 2a-8h

Topical Formulations

Different quantities of artesunate (see Table 1) were incorporated into the various bases. In part surface-active substances were also added to the formulations.

TABLE 1

| Example No. | Artesunate (in g) | Additives | Base q.s. ad 100 g |
|---|---|---|---|
| 2a-2h | 2a: 0.1<br>2b: 0.5<br>2c: 1.0<br>2d: 5.0<br>2e: 10.0<br>2f: 15.0<br>2g: 30<br>2h: 40 | — | White Petrolatum |
| 3a-3h | 3a: 0.1<br>3b: 0.5<br>3c: 1.0<br>3d: 5.0<br>3e: 10.0<br>3f: 15.0<br>3g: 30<br>3h: 40 | Polysorbate 0.5 g;<br>Macrogol 2000-<br>Stearate 0.5 g<br>PEG-40-Sorbitan<br>Peroleate 0.5 g | White Petrolatum |
| 4a-4h | 4a: 0.1<br>4b: 0.5<br>4c: 1.0<br>4d: 5.0<br>4e: 10.0<br>4f: 15.0<br>4g: 30<br>4h: 40 | | Beeswax |
| 5a-5h | 5a: 0.1<br>5b: 0.5<br>5c: 1.0<br>5d: 5.0<br>5e: 10.0<br>5f: 15.0<br>5g: 30<br>5h: 40 | soya lecithin 2 g | Paraffin |
| 6a-6h | 6a: 0.1<br>6b: 0.5<br>6c: 1.0<br>6d: 5.0<br>6e: 10.0<br>6f: 15.0<br>6g: 30<br>6h: 40 | Macrogol 2000-<br>Stearate 2 g | Rapeseed oil |
| 7a-7h | 7a: 0.1<br>7b: 0.5<br>7c: 1.0<br>7d: 5.0<br>7e: 10.0<br>7f: 15.0 | Isopropyl myristate 1 g | Decamethyl cyclo-<br>pentasiloxane (19 g)<br>Silicone elastomer<br>gel (ad 100 g) |
| 8a-8h | 8a: 0.1<br>8b: 0.5<br>8c: 1.0<br>8d: 5.0<br>8e: 10.0<br>8f: 15.0 | | Decamethyl cyclo-<br>pentasiloxane (25 g)<br>Mineral oil ad 100 g |

EXAMPLES 9a-9i

Topical (Cutaneous) Applications in the Treatment or Prevention of Pigmented Moles a) A 13-year old boy with a raised dark-brown birthmark (dysplastic nevus cell nevus) on the chest, with uneven structure approx 1.2 cm in diameter was treated 2-3 times per week with the 10% artesunate petrolatum ointment from Example 2a. After 2 weeks the birthmark was light brown with a few dark small punctiform spots which looked like "crystallized" coloring matter. The birthmark is dry and flaking and looks as though it is receding from the "inside".

b) A woman with 3 black birthmarks raised over the surface of the skin (junction nevi on the trunk) with a diameter of 0.5 to 1.0 cm applied the 10% artesunate petrolatum ointment from Example 2a 3 times per week under occlusion (as a plaster) overnight. After one week a dark spot was discernible in each birthmark. After 3 weeks the skin flaked off together with this dark crystal-like formations. Three pale birthmarks remained, with pigment-free places, which are no longer raised above the surface of the skin. A continuation of the treatment leads to a further fading and flaking of the skin at the treated locations.

c) Treatment of 2 nevus cell nevus precursors, that is extravasated raised areas of the skin with a diameter of 0.3-0.4 cm: A three time application of the plaster with the 10% artesunate ointment from Example 2a overnight after two weeks led to a change in color, light red formation with dark spots. The raised, changed area of the skin could be detached. Two small wounds remained, due to detachment too early, which healed.

d) A female test subject with a nevus of approx. 3-4 cm in diameter (basiloma) applied the 10% artesunate ointment from Example 1 over 3 months (cyclically, in the evening, every other week). Initially the nevus exhibited a redness (similar to inflammation process). After 3 months a recession (in terms of color and structure) could be seen of approx. 90%. After approx. 5 months the nevus was no longer visible.

e) A female test subject with a nevus on her arm (unction nevus) likewise applied the 10% artesunate ointment from Example 1. Since the test subject was not monitored, no precise data can be given here on the frequency of application; however, the application of the ointment extended over several weeks. The nevus is hardly visible today.

f) A 13-year old male test subject with a congenital nevus in the root of the nose/eye area applied the 10% artesunate ointment from Example 1 twice to three times a week under occlusion (plaster) for two months. At first the nevus exhibited many small dark spots. It reacts more slowly. However, initial successes are already indicated. Overall it has become much paler and exhibits several skin-colored areas.

g) A 13-year old female patient with a dermal nevus applied the 10% artesunate ointment from Example 1 for 3 days. An immediate concentration with the formation of 3 dark spots in the nevus occurred and the remaining area is virtually colorless.

h) A female test subject applied the 10% artesunate ointment from Example 1 twice (once each on 2 consecutive days) over a large area on the abdomen, where she already had numerous nevus cell nevi (unction nevi). In addition to the existing nevi, red, in part nevus precursors of the type described at the outset already became visible on the $2^{nd}$ day of treatment in the form of tiny dots that were unevenly distributed over the treated areas. These nevus precursors were already in existence, but were made visible only by the treatment with the ointment. After 2-3 days they became dark to black. In part they looked like dark crystals sitting in pores. They flaked off within 2-3 weeks with the upper stratum corneum layer or detached if scratched a little with a fingernail.

i) A female test subject treated the backs of her hands, on which she had numerous pigmented moles (nevi) of differing sizes, with the ointment from Example 1. The existing nevi and nevus precursors faded rapidly and receded with increasing duration of application (7 or 10 days). The color of the pigmented moles became lighter after the treatment was discontinued. After four weeks they were hardly to not at all visible.

EXAMPLE 10

Topical Application in the Treatment of Nail Fungal Infections

Nail fungal infections on the middle and big toes: half of the nail on the big toe infected. The treatment with conventional agents such as Lamisil had little success. The 10% artesunate petrolatum ointment from Example 2a was applied 3-4 times a week. The ointment was applied above all to the nail bed and under the nail. Already after 2 weeks a distinct improvement could be observed. After 4 weeks the discoloration on the middle toe had completely disappeared or had grown out. The necrotic nail portion on the big toe crumbled off. The treatment of the remaining nail was easier and more effective. The active agent reached the border region to the healthy portion of the nail unhindered. The nail growing in is fine, has no pale discoloration. In the case of fungal infections particularly of the nails, it can be expected that no additional systemic treatment with antimycotics will be necessary and thus not only the cost but also the risk of side effects of the antimycotic treatment will be reduced.

What is claimed is:

1. A method of treating at least one benign pigmented mole, wherein the method comprises locally applying to a subject in need thereof one or more compounds of formula (I):

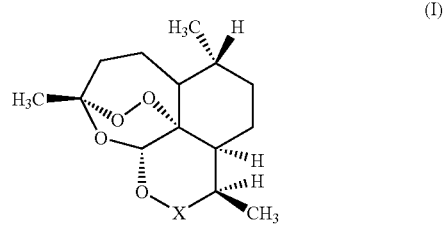

wherein:
X represents CO, CHOZ or CHNRZ;
Z is selected from hydrogen; straight-chain and branched ($C_1$-$C_6$) alkyl; straight-chain or branched ($C_2$-$C_6$) alkenyl; straight-chain or branched ($C_2$-$C_6$) alkynyl; ($C_3$-$C_8$) cycloalkyl; ($C_6$-$C_{24}$) aryl; ($C_7$-$C_{24}$) aralkyl; m- and p-$CH_2(C_6H_4)$COOM; $COR^3$; $CSR^3$; $C(NR^6)R^3$; $SOR^4$; $SO_2OM$; $SO_2NR^7R^8$; $SO_2O$-artemisinyl; $SO_2NH$-artemisinyl; $POR^4R^5$; and $PSR^4R^5$;

$R^3$ is selected from straight-chain or branched ($C_1$-$C_6$) alkyl; straight-chain or branched ($C_1$-$C_6$) alkoxy; straight-chain or branched ($C_2$-$C_6$) alkenyl; straight-chain or branched ($C_2$-$C_6$) alkynyl; ($C_3$-$C_8$) cycloalkyl; ($C_6$-$C_{24}$) aryl; ($C_6$-$C_{10}$) aryloxy; ($C_7$-$C_{24}$) aralkyl; —($CH_2$)$_n$—COOM, with n being an integer of from 1 to 6; and 10α-di-hydroartemisinyl;

$R^4$ and $R^5$ are independently selected from straight-chain or branched ($C_1$-$C_6$) alkyl; straight-chain or branched ($C_2$-$C_6$) alkenyl; straight-chain or branched ($C_2$-$C_6$) alkynyl; ($C_3$-$C_8$) cycloalkyl; ($C_6$-$C_{24}$) aryl; ($C_7$-$C_{24}$) aralkyl; OM; straight-chain or branched ($C_1$-$C_6$) alkoxy; ($C_6$-$C_{10}$) aryloxy; and $NR^7R^8$;

$R^6$ is selected from straight-chain or branched ($C_1$-$C_6$) alkyl; straight-chain or branched ($C_2$-$C_6$) alkenyl; straight-chain or branched ($C_2$-$C_6$) alkynyl; ($C_3$-$C_8$) cycloalkyl; ($C_6$-$C_{24}$) aryl; and ($C_7$-$C_{24}$) aralkyl;

M represents hydrogen or a pharmaceutically acceptable cation;

$R^7$ and $R^8$ are independently selected from straight-chain or branched ($C_1$-$C_6$) alkyl, or $R^7$ and $R^8$ together form a ($C_4$-$C_6$) alkylene bridge; and R is selected from hydrogen; straight-chain or branched ($C_1$-$C_6$) alkyl; straight-chain or branched ($C_2$-$C_6$) alkenyl; straight-chain or branched ($C_2$-$C_6$) alkynyl; ($C_3$-$C_8$) cycloalkyl; ($C_6$-$C_{24}$) aryl; and ($C_7$-$C_{24}$) aralkyl.

2. The method of claim 1, wherein the one or more compounds of formula (I) are applied in a form of a topical formulation.

3. The method of claim 2, wherein the topical formulation comprises at least one of a paste, an ointment, a suspension, a solution, a gel, a spray, and a cream.

4. The method of claim 3, wherein the topical formulation comprises an ointment and loss of moisture from skin is prevented by application of the ointment.

5. The method of claim 2, wherein the topical formulation is applied in conjunction with a plaster.

6. The method of claim 1, wherein the at least one benign pigmented mole is selected from one or more of acquired nevus cell nevi; congenital nevus cell nevi, disorders of melanin pigmentation, and pigmented moles of the mucous membranes.

7. The method of claim 6, wherein the at least one benign pigmented mole comprises an acquired nevus cell nevi.

8. The method of claim 6, wherein the at least one benign pigmented mole comprises a congenital nevus cell nevi.

9. The method of claim 6, wherein the at least one benign pigmented mole is selected from one or more of birthmarks, liver spots, sun spots and age spots.

10. The method of claim 1, wherein the one or more compounds of formula (I) comprise at least one compound wherein X is CHOZ, Z is selected from m- and p-$CH_2(C_6H_4)$COOM and $COR^3$; and $R^3$ represents —($CH_2$)$_n$—COOM.

11. The method of claim 1, wherein the one or more compounds of formula (I) comprise at least one compound selected from artemisinine; dihydroartemisinine; carboxyl group containing derivatives of formula (I); artemether; arteether; propyl carbonate of dihydroartemisinine, and artelinic acid.

12. The method of claim 11, wherein the one or more compounds of formula (I) comprise at least one compound selected from artemisinine, dihydroartemisinine, and artesunate.

13. The method of claim 11, wherein the one or more compounds of formula (I) comprise artesunate.

* * * * *